(12) United States Patent
Zhang

(10) Patent No.: US 11,607,124 B2
(45) Date of Patent: Mar. 21, 2023

(54) SYSTEM AND METHOD FOR MEASURING PUPILLARY DISTANCE

(71) Applicant: SHANGHAI TRUTHVISION INFORMATION TECHNOLOGY CO., LTD., Shanghai (CN)

(72) Inventor: Zhong Zhang, Great Falls, VA (US)

(73) Assignee: SHANGHAI TRUTHVISION INFORMATION TECHNOLOGY CO., LTD., Shanghai (CN)

( * ) Notice: Subject to any disclaimer, the term of this patent is extended or adjusted under 35 U.S.C. 154(b) by 573 days.

(21) Appl. No.: 16/662,733

(22) Filed: Oct. 24, 2019

(65) Prior Publication Data

US 2020/0054209 A1 Feb. 20, 2020

Related U.S. Application Data

(63) Continuation of application No. PCT/US2017/029122, filed on Apr. 24, 2017.

(51) Int. Cl.
*A61B 3/11* (2006.01)
*G02B 27/01* (2006.01)
(Continued)

(52) U.S. Cl.
CPC ............. *A61B 3/111* (2013.01); *A61B 3/11* (2013.01); *A61B 3/145* (2013.01); *G02B 27/017* (2013.01);
(Continued)

(58) Field of Classification Search
CPC ............. A61B 3/111; G06T 7/10; G06T 7/12
(Continued)

(56) References Cited

U.S. PATENT DOCUMENTS 5,291,560 A * 3/1994 Daugman ............ A61B 3/1216
382/222
6,095,650 A * 8/2000 Gao ..................... G02C 13/003
351/227

(Continued)

FOREIGN PATENT DOCUMENTS

CN 102278978 A 12/2011
CN 105380592 A 3/2016

OTHER PUBLICATIONS

Timm F., Barth E. Accurate Eye Centre Localisation by Means of Gradients; Proceedings of the International Conference on Computer Theory and Applications (VISAPP); Algarve, Portugal. Mar. 5-7, 2011; pp. 125-130 (Year: 2011).*

(Continued)

*Primary Examiner* — Zachary W Wilkes
(74) *Attorney, Agent, or Firm* — Metis IP LLC

(57) ABSTRACT

A method implemented on a computing device having at least one processor, storage, and a communication platform connected to a network may include: obtaining a head image of a user with one or more dimension indicators, determining an eye region in the head image of the user and determining a pupillary distance of the user based on the one or more dimension indicators and the determined eye region. A method implemented on a computing device having at least one processor, storage, and a communication platform connected to a network may include: receiving a request at a user terminal, recording a video of a user wearing a wearable device with the user terminal, determining a pupillary distance of the user based on the video and synchronously displaying the pupillary distance on the video of the user during recording. The wearable device may include one or more dimension indicators.

6 Claims, 16 Drawing Sheets

(51) Int. Cl.
*G06T 7/10* (2017.01)
*A61B 3/14* (2006.01)
(52) U.S. Cl.
CPC ........ *G06T 7/10* (2017.01); *G02B 2027/0178* (2013.01)
(58) Field of Classification Search
USPC .......................................................... 351/204
See application file for complete search history.

(56) References Cited

U.S. PATENT DOCUMENTS

| | | | |
|---|---|---|---|
| 6,535,223 B1 | 3/2003 | Foley | |
| 7,287,853 B2 | 10/2007 | Toshima et al. | |
| 7,665,843 B2* | 2/2010 | Xie | G06Q 30/0603 351/159.75 |
| 7,869,626 B2* | 1/2011 | Ko | G06V 40/193 382/117 |
| 8,459,792 B2* | 6/2013 | Wilson | G06T 7/60 351/204 |
| 9,091,867 B1* | 7/2015 | Farache | G02C 13/005 |
| 9,183,439 B2* | 11/2015 | Lefebvre | G06V 40/193 |
| 9,236,024 B2 | 1/2016 | Coon | |
| 10,222,634 B2* | 3/2019 | Teodorovic | G02C 7/027 |
| 10,417,495 B1* | 9/2019 | Davami | G06V 40/19 |
| 2013/0076884 A1* | 3/2013 | Choukroun | H04N 5/23219 348/78 |
| 2015/0055086 A1* | 2/2015 | Fonte | G02C 13/005 700/98 |
| 2015/0154322 A1 | 6/2015 | Fonte et al. | |
| 2017/0134643 A1* | 5/2017 | Kim | G06V 40/19 |
| 2018/0168446 A1* | 6/2018 | Kim | G06V 40/45 |
| 2018/0199810 A1* | 7/2018 | Li | A61B 3/14 |

OTHER PUBLICATIONS

International Search Report in PCT/US2017/029122 dated Jul. 13, 2017, 2 pages.
Written Opinion in PCT/US2017/029122 dated Jul. 13, 2017, 6 pages.

* cited by examiner

SYSTEM AND METHOD FOR MEASURING PUPILLARY DISTANCE

CROSS REFERENCE CROSS REFERENCE TO RELATED APPLICATIONS

This application is a Continuation of International Application No. PCT/US2017/029122 filed on Apr. 24, 2017, the entire contents of which are hereby incorporated by reference.

TECHNICAL FIELD

This application relates to a measuring system and, more particularly, relate to a system for measuring pupillary distance with a user terminal.

BACKGROUND

Current online business of prescription glasses is limited in large part because a user needs to visit an optometrist to receive a prescription with accurate pupillary distance measurement before purchasing. That may introduce extra costs for the glasses purchasing. In addition, existing virtual wearing technologies may not be able to measure one or more sizes related to a user's head. An online prescription glasses provider has difficulty to recommend the glasses that fits a user's head and/or facial character. The actual frame that arrives after ordering online may not provide exact fit as the virtual wearing shows. It is necessary to provide a system and method to tackle the above addressed problems and satisfy these demands from the user.

SUMMARY

According to a an aspect of the present disclosure, a method implemented on a computing device having at least one processor, storage, and a communication platform connected to a network may include: obtaining a head image of a user with one or more dimension indicators, determining an eye region in the head image of the user and determining a pupillary distance of the user based on the one or more dimension indicators and the determined eye region.

In some embodiments, the method may further include: obtaining one or more measurements associated with the head of the user from the head image, determining an image scale based on the one or more dimension indicators and the one or more measurements and determining one or more parameters associated with sizes of a glasses frame.

In some embodiments, the determining the eye region in the head image of the user may include: locating an eye image including two eyes in the head image of the user, segmenting the eye image from the head image, identifying an iris region and a sclera region for each eye in the eye image and determining a pupillary center of each eye based on the iris region and the sclera region.

In some embodiments, the one or more indicators may be implemented on a wearable device worn by the user.

In some embodiments, the one or more measurements parameters may include at least one of a width of face or a distance between an outer end of each eye and an ear on the same side of the face.

In some embodiments, the determining the image scale based on the one or more dimension indicators and the one or more measurements may include: determining information associated with the one or more dimension indicators and determining the image scale based on the information of the one or more dimension indicators and the one or more measurements. The information associated with the one or more dimension indicators may include at least one of color information and symmetry information.

In some embodiments, the determining the pupillary center of each eye based on the iris region and the sclera region may include: determining a plurality of edge points between the iris region and the sclera region for each eye, each of the plurality of edge points having a gradient direction, forming a line based on each of the plurality of edge points and its gradient direction, determining a plurality of cross points, each cross point formed by a pair of lines and determining a pupillary center based on the plurality of cross points.

In some embodiments, the wearable device may include a pair of glasses made of paper.

According to a another aspect of the present disclosure, a method implemented on a computing device having at least one processor, storage, and a communication platform connected to a network may include: receiving a request at a user terminal, recording a video of a user wearing a wearable device with the user terminal, determining a pupillary distance of the user based on the video and synchronously displaying the pupillary distance on the video of the user during recording. The wearable device may include one or more dimension indicators.

In some embodiments, the method may further include: obtaining each image of the user with the one or more dimension indicators from the video, determining a per-image pupillary distance of the user based on the each image of the user and determining a pupillary distance of the user based on the per-image pupillary distances for all images in the video.

In some embodiments, the method may further include: determining one or more measurements associated with a pair of prescription glasses based on the video and synchronously displaying the one or more measurements on the video of the user during recording.

In some embodiments, the wearable device may include a pair of glasses made of paper.

According to another aspect of the present disclosure, a system may include at least one computer-readable storage medium including a set of instructions for migrating data records, a communication platform connected to a network and at least one processor in communication with the computer-readable storage medium. When executing the set of instructions, the at least one processor may be directed to: obtain a head image of a user with one or more dimension indicators, determine an eye region in the head image of the user and determine a pupillary distance of the user based on the one or more dimension indicators and the determined eye region.

According to another aspect of the present disclosure, a system may include at least one computer-readable storage medium including a set of instructions for migrating data records, a communication platform connected to a network and at least one processor in communication with the computer-readable storage medium. When executing the set of instructions, the at least one processor may be directed to: receive a request at a user terminal, record a video of a user wearing a wearable device with the user terminal, determine a pupillary distance of the user based on the video and synchronously display the pupillary distance on the video of the user during recording. The wearable device may include one or more dimension indicators.

According to another aspect of the present disclosure, a non-transitory computer-readable medium may include at least one set of instructions for migrating data records. When executed by at least one processor, the at least one set of instructions may direct the at least one processor to: obtain a head image of a user with one or more dimension indicators, determine an eye region in the head image of the user and determine a pupillary distance of the user based on the one or more dimension indicators and the determined eye region.

According to another aspect of the present disclosure, a non-transitory computer-readable medium, comprising at least one set of instructions for migrating data records. When executed by at least one processor, the at least one set of instructions may direct the at least one processor to: receive a request at a user terminal, record a video of a user wearing a wearable device with the user terminal, determine a pupillary distance of the user based on the video and synchronously display the pupillary distance on the video of the user during recording. The wearable device may include one or more dimension indicators.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "unit," "module," and/or "engine" used herein are one method to distinguish different components, elements, parts, section or assembly of different level in ascending order. However, the terms may be displaced by other expression if they may achieve the same purpose.

It will be understood that when a unit, module or engine is referred to as being "on," "connected to" or "coupled to" another unit, module, or engine, it may be directly on, connected or coupled to, or communicate with the other unit, module, or engine, or an intervening unit, module, or engine may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Figure 1:
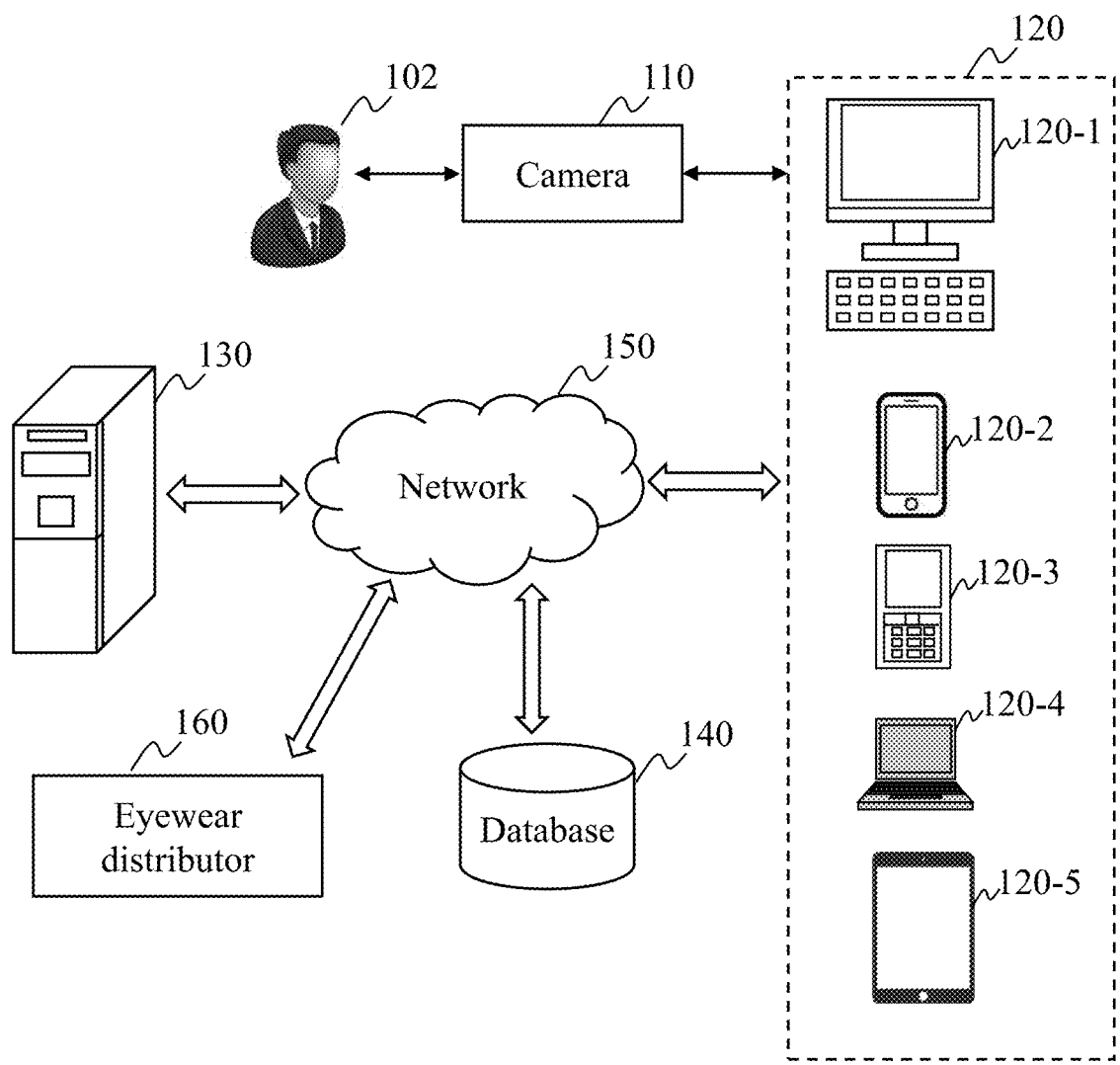
FIG. 1 is a schematic diagram illustrating an exemplary measuring system according to some embodiments of the present disclosure.

FIG. 1 is a schematic diagram illustrating an exemplary measuring system 100 according to some embodiments of the present disclosure. The measuring system 100 may include a camera 110, a user terminal 120, a processing device 130 (also referred as server 130), a database 140, a network 150, and an eyewear distributor 160.

The camera 110 may record a video and/or an image of a user 102. The video and/or image may include real-time captured information of the user 102. For example, the information may include a real-time captured video having a plurality of head images of the user 102. In some embodiment, the camera 110 may be integrated in the user terminal 120.

The user terminal 120 may receive, output, display, and/or process information. For example, the user terminal 120 may receive information from the camera 110, the processing device 130, the database 140, the network 150, the eyewear distributor 160, etc. As another example, the user terminal 120 may output or display information (e.g., a video of the user with a pupillary distance dynamically displayed thereon) to a user (e.g., user 102). As still another example, the user terminal 120 may process information received from the camera 110, the processing device 130, the database 140, the network 150, the eyewear distributor 160, etc.

In some embodiments, the user terminal 120 may determine pupillary centers of a user and an image scale of a head image captured by the camera 110. A pupillary distance may be determined based on the pupillary center and the image scale.

In some embodiments, the user terminal 120 may include a desktop computer 120-1, a mobile device 120-2, a personal digital assistance 120-3, a laptop computer 120-4, a tablet computer 120-5, or the like, or any combination thereof. In some embodiments, the mobile device 120-2 may include a smart home device, a wearable device, a smart mobile device, a virtual reality device, an augmented reality device, or the like, or any combination thereof. In some embodiments, the smart home device may include a smart lighting device, a smart television, a smart video camera, an interphone, or the like, or any combination thereof. In some embodiments, the wearable device may include a smart bracelet, a smart footgear, a smart glass, a smart watch, a smart helmet, a smart clothing, a smart backpack, a smart accessory, or the like, or any combination thereof. In some embodiments, the smart mobile device may include a smartphone, a gaming device, a navigation device, a point of sale (POS) device, or the like, or any combination thereof.

The processing device 130 may process information and/or data relating to measurements to perform one or more functions described in the present disclosure. For example, the processing device 130 may further process information transmitted from and/or received at the user terminal 120. For example, the processing device 130 may include a central processing unit (CPU), an application-specific integrated circuit (ASIC), an application-specific instruction-set processor (ASIP), a graphics processing unit (GPU), a physics processing unit (PPU), a digital signal processor (DSP), a field programmable gate array (FPGA), a programmable logic device (PLD), a controller, a microcontroller unit, a reduced instruction-set computer (RISC), a microprocessor, or the like, or any combination thereof. In some embodiments, the processing device 130 may be integrated in the user terminal 120.

The database 140 may acquire and/or store information of the components (e.g., the camera 110, the terminal 120, or the processing device 130, etc.) of the measuring system 100. For example, the database 140 may acquire information from the user terminal 120. In some embodiments, the information acquired and/or stored may include programs, software, algorithms, functions, files, parameters, data, texts, numbers, images, or the like, or any combination thereof. For of example, the database 140 may store images with different formats including, for example, bmp, jpg, png, tiff, gif, pcx, tga, exif, fpx, svg, psd, cdr, pcd, dxf, ufo, eps, ai, raw, WMF, or the like, or any combination thereof. In some embodiments, the database 140 may store parameters (e.g., a pupillary distance, a glasses frame size, etc.) from the user terminal 120. In some embodiments, the database 140 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary mass storage may include a magnetic disk, an optical disk, a solid-state drives, etc.

The network 150 may facilitate exchange of information. In some embodiments, one or more components in the measuring system 100 (e.g., the camera 110, the terminal 120, the processing device 130, the database 140, and the eyewear distributor 160) may send information to other component(s) in the measuring system 100 via the network 150. For example, the eyewear distributor 160 may obtain parameters (e.g., a pupillary distance) for prescription glasses from the user terminal 120 via the network 150. In some embodiments, the network 150 may be any type of a wired or wireless network, or a combination thereof. Merely by way of example, the network 150 may include a cable network, a wire line network, an optical fiber network, a telecommunication network, an intranet, an Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof.

The eyewear distributor 160 may recommend one or more pairs of prescription glasses. In some embodiments, the eyewear distributor 160 may receive information of the prescription glasses from the user terminal 120. The information may include a width of a user's face, a pupillary distance, a glasses frame size (e.g., a temple length of glasses), etc.

It should be noted that the description above in relation to the measuring system 100 is provided for the purposes of illustration, and not intended to limit the scope of the present disclosure. For persons having ordinary skills in the art, various variations and modifications may be conducted under the guidance of the present disclosure. However, those variations and modifications do not depart the scope of the present disclosure. For example, the camera 110 may be integrated in the user terminal 120.

Figure 2:
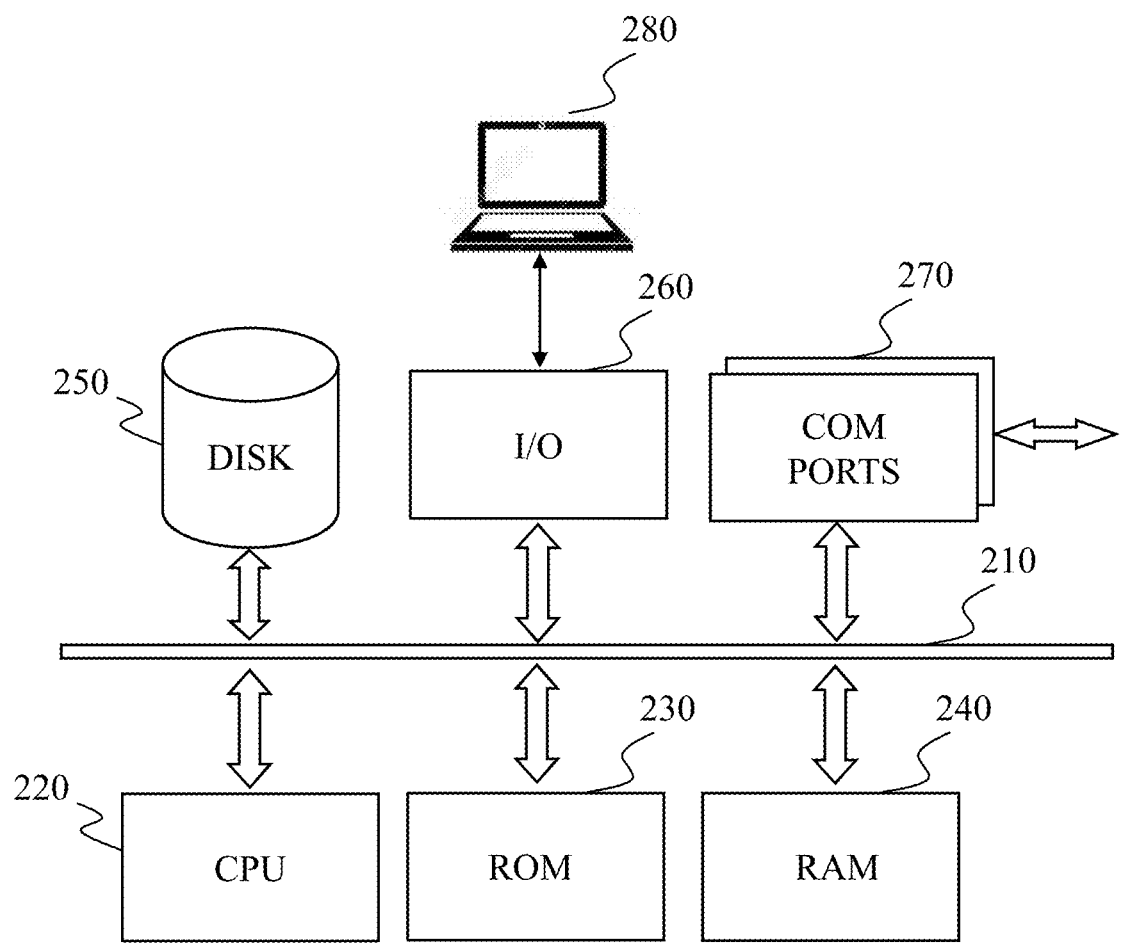
FIG. 2 is a device diagram illustrating an exemplary computing device on which the measuring system may be implemented according to some embodiments of the present disclosure.

FIG. 2 is a device diagram illustrating an exemplary computing device 200 on which the measuring system can be implemented according to some embodiments in the present disclosure. The system incorporating the present disclosure has a functional block diagram illustration of a hardware platform which includes user interface elements. The computer may be a general purpose computer or a special purpose computer. Both can be used to implement a system for the present disclosure. The computing device 200 may be used to implement any component of device connecting the measuring system 100 and perform one or more functions thereof as described herein. For example, the user terminal 120 may be implemented on the computing device 200, via its hardware, software program, firmware, or a combination thereof. Although only one such computer is shown, for convenience, the computer functions relating to measurements as described herein may be implemented in a distributed manner on a number of similar platforms, to distribute the processing load. In some embodiments, the computing device 200 may be used as the user terminal 120 disclosed in FIG. 1.

The computing device 200, for example, may include communication (COM) ports 270 to facilitate communications between the computing device 200 and other devices via, for example, a network (wired or wireless). The computing device 200 may also include a central processing unit (CPU) 220, in the form of one or more processors, for executing program instructions. The computing device 200 may include an internal communication bus 210, program storage, and data storage of different forms, e.g., disk 250, read only memory (ROM) 230, or random access memory (RAM) 240, for various data files to be processed and/or communicated by the computing device 200, as well as possibly program instructions to be executed by the CPU 220. The computing device 200 may also include an I/O component 260, supporting input/output flows between the computing device 200 and other components therein such as user interface element 280. The computing device 200 may also receive programming and data via network communications.

Figure 3:
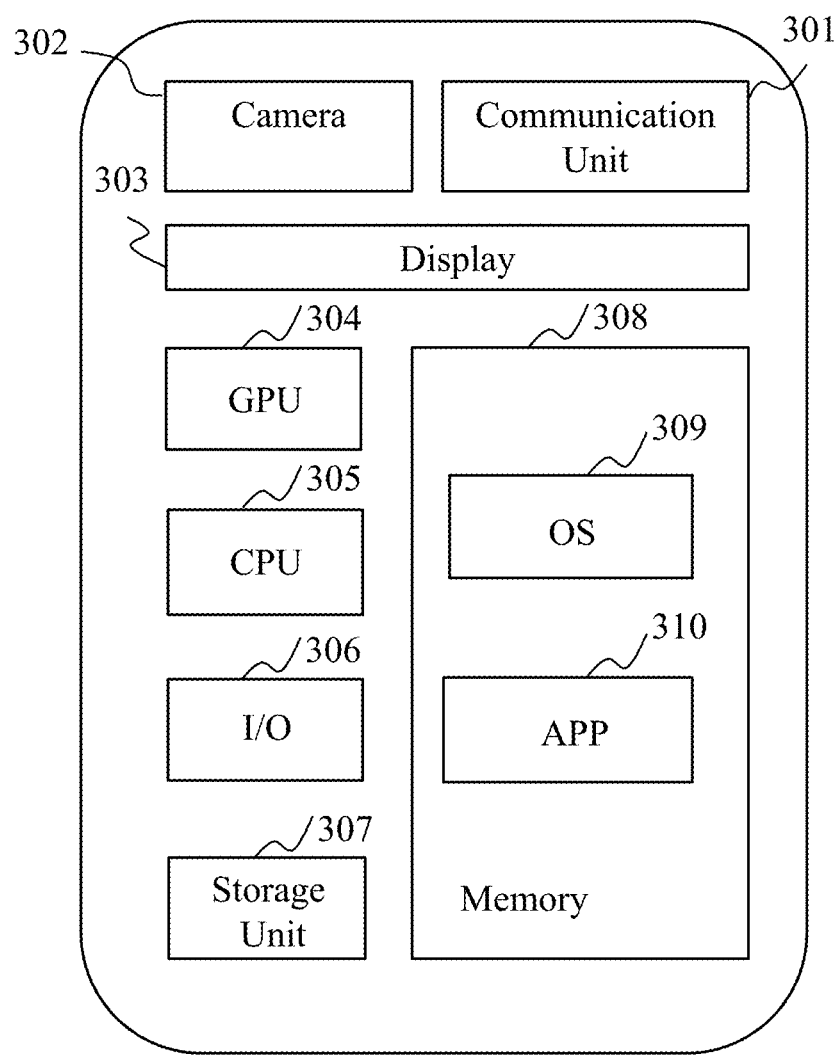
FIG. 3 is a block diagram illustrating an exemplary computing device on which user terminal and/or processing device may be implemented according to some embodiments of the present disclosure.

FIG. 3 is a block diagram illustrating an exemplary computing device 300 on which user terminal 120 and/or processing device 130 may be implemented according to some embodiments of the present disclosure. For example, the user terminal 120 may be implemented on the computing device 300 and configured to perform functions of the user terminal 120.

The computing device 300 may be a mobile device which may be used to implement any component of device connecting the measuring system 100 and perform one or more functions thereof as described herein. For example, the user terminal 120 may be implemented on the computing device 300, via its hardware, software program, firmware, or a combination thereof. The computing device 300 may be a smart phone, a laptop computer, a music player, a gaming device, a global positioning system (GPS) device, a wearable device (e.g., a smart glass or a smart glass), or other electronic terminal as described elsewhere in the present disclosure.

The computing device 300, for example, may include a central processing unit (CPU) 305, a graphics processing unit (GPU) 304, a display component 303, a memory 308, a communication unit 301, a camera 302, a storage unit 307, and an I/O component 306. Any suitable component, for example, a bus or a controller, may also be incorporated into the computing device 200. As illustrated in FIG. 3, an operating system (OS) 309 and/or an application (App) 310 may be loaded in memory 308 and executed by the CPU 305. The OS 309 may include an iOS system, Android system, Windows Phone system, or the like, or any combination thereof. The App 310 may include one or more mobile apps that can be implemented on the OS 309, such as a browser or an application implemented in the computing device 300 for information processing. The communication unit 301 may be an antenna component configured to receive/send information. The camera 302 may be configured to perform functions of the camera 110.

In some embodiments, the display component 303 and/or the I/O component 306 of the computing device 300 in FIG. 3 may have the same structures, functions, and/or types as the description of the user interface element 280 and/or the I/O component 260 of the computing device 200 in FIG. 2, respectively.

The method and/or processes of the present disclosure may be implemented as the program instructions. In some embodiments, the CPU 305 may be a main controller of the computing device 300. The CPU 305 may control every component in the computing device 300, and connect them with each other to allow coordination with each other. In some embodiments, the CPU 305 may control the I/O component 306 to input or output information (e.g., a pupillary distance), wherein the control may include power control, transmitting rate control, inputting/outputting information size control, etc. In some embodiments, the CPU 305 may control the display 303 to work in determined modes. And the control of the display 303 may include display quality control, display time control, display rate control, display switchover control, etc. In some embodiments, CPU 305 may control the memory 308 or the storage unit 309 to store data. The control of the memory 308 or the storage unit 309 may include storing mode control, storing rate control, storage format control, storage life control. In some embodiments, the CPU 305 may control other internal components in computing device 300, and it may process the data and/or instructions transmitting between different components. In some embodiments, the CPU 305 may control the camera 302 to record videos and/or images.

Figure 4:
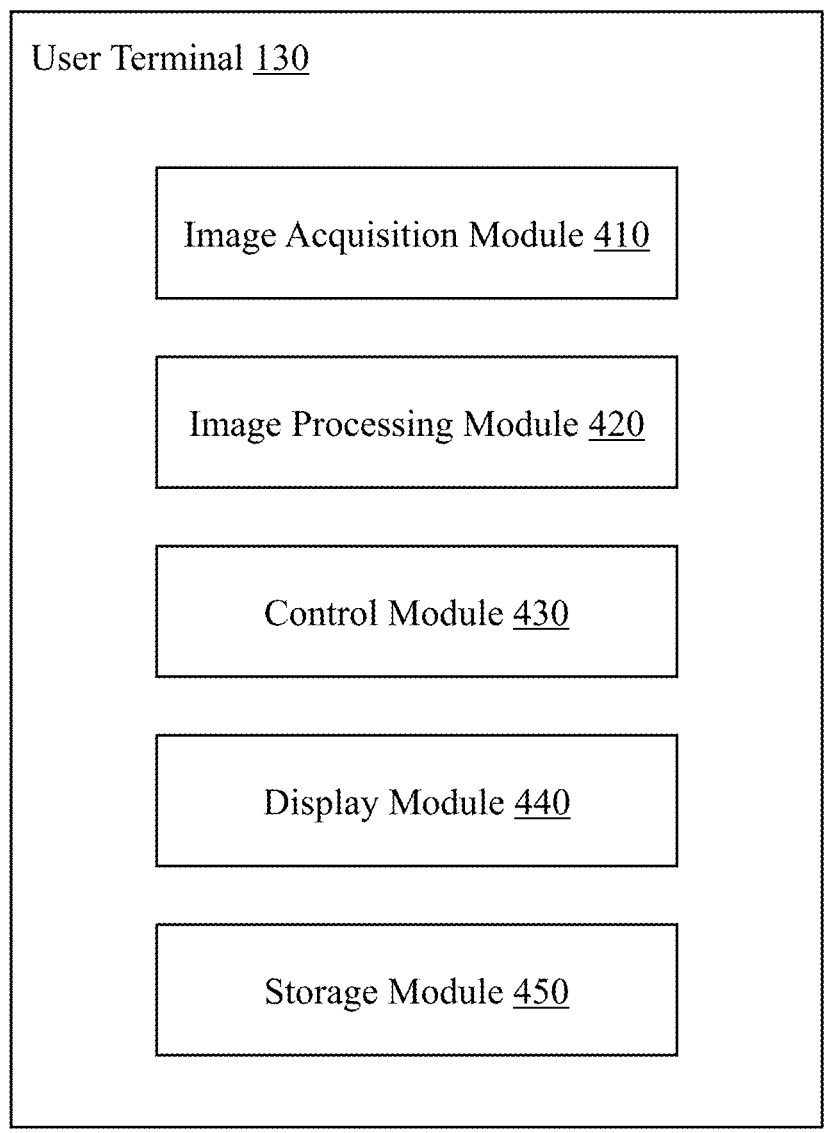
FIG. 4 is a block diagram illustrating an exemplary user terminal according to some embodiments of the present disclosure.

FIG. 4 is a block diagram illustrating an exemplary user terminal 120 according to some embodiments of the present disclosure. The user terminal 120 may be configured to determine a pupillary distance of an object based on a video recorded for the object. The user terminal 120 may include an image acquisition module 410, an image processing module 420, a control module 430, a display module 440, and a storage module 450. The modules included in the user terminal 120 may be connected in a wired or wireless manner.

The image acquisition module 410 may be configured to acquire one or more images of the object from the video, each of which is used to determine a pupillary distance of the object or other related parameters. For example, an image including eyes on a face of a person may be acquired by the image acquisition module 410 and used to determine a pupillary distance of the person. In some embodiments, a plurality of images corresponding to the same face of the person may be acquired. The image acquisition module 410 may determine an average pupillary distance of the person based on the plurality of images. In some embodiments, the image acquisition module 410 may dynamically extract a plurality of fames (i.e., images) from a real-time video recording of the person to determine the pupillary distance of the person.

In some embodiments, the one or more images may be in a form of digital data. The digital data may be generated by the camera 110 connected with the user terminal 120, or by the camera 302 integrated in the user terminal 120. The camera may capture a head image of a person in response to an instruction transmitted from the user terminal 120. As in another example, the camera may record a video of the person in response to an instruction transmitted from the user terminal 120. In some embodiments, the digital data may be transmitted to the database 140 via the network 150. For example, a database of a civil administration department may contained all residents' head images for purposes such as producing ID cards. The database of the civil administration department may transmit a head image of a residence in response to an instruction transmitted from the user terminal 120 residing in a local department of motor vehicles (DMV).

The image processing module 420 may be configured to process the image acquired by the image acquisition module 410. In some embodiments, the processing may include transforming image format, adjusting image quality, recognizing specific symbols, identifying specific region, segmenting the image, calculating pixel values, or the like, or a combination thereof. For example, an image may be acquired by the image acquisition module 410 from the database 140. The quality of the image may not be sufficiently good for further processing because of the storage format of which. The quality of the image may be improved by performing the image format transforming process. As another example, to determine a pupillary distance of a person showing on the image, the image processing module 420 may need to perform the region identifying process to determine locations of eyes on the image. Details of the image processing module 420 may be disclosed elsewhere in the present disclosure (e.g., in the description of FIG. 4).

The control module 430 may be configured to generate one or more instructions to operate one or more modules of the user terminal 120. The one or more instructions may include an instruction to operate the camera to take a photo, an instruction to operate the camera to record a video, an instruction to operate the image processing module 420 to adjust processing algorithms, an instruction to control display parameters applied on the display module 440, an instruction to operate the storage module 450 to storage data, or the like, or a combination thereof. Input devices (e.g., a touchscreen, a keyboard, and a voice input device) may be included in the control module 430 (not shown in FIG. 4). For example, a keyboard may be integrated in the user terminal 120. An instruction may be generated in response to pressing down a plurality of keys on the keyboard in a certain sequence by a user. In some embodiments, the instruction may direct the camera 110 to take a photo or to record a video. In some embodiments, the instruction may direct the display module 440 to display the photo or to play a real-time recording by the camera 110. In some embodiments, the instruction may direct the storage module 450 to storage data. For example, after a pupillary distance is determined, the storage module 450 may receive an instruction to store the pupillary distance data together with the corresponding video including a plurality of head images and some other related data (e.g., user ID, time information, location information).

The display module 440 may include one or more display devices configured to present a variety of content including text content, audio content, static images, or real-time recordings. Alternatively or additionally, the display module 440 may be communicatively coupled to the one or more display devices. Exemplary display devices may include but not limit to a liquid crystal display (LCD), a light emitting diode (LED)-based display, a flat panel display or curved screen, a television device, a cathode ray tube (CRT), the like, or a combination thereof. In some embodiments, at least one of the one or more display devices may be capable of displaying the content in a three-dimensional form. In some embodiments, the one or more display devices may include a touchscreen (e.g., a mobile phone with a touch screen). In some embodiments, the content displayed on the display devices may be overlaid by one or more characters, geometric patterns or numbers. For example, when a head image of a person is displayed on the display devices, a straight line with two endpoints indicating the locations of two pupils of the person may be overlaid on the head image. As another example, when a real-time video is played on the display devices, the two endpoints of the straight line indicating the locations of two pupils may move dynamically according to the movement of the head in the real-time video. The length of the straight line may represent the pupillary distance. In some embodiments, a number indicating the pupillary distance may be displayed together with the straight line. When the real-time video is played on the display devices, the number indicating the pupillary distance may update dynamically according to the movement of the head in the real-time video.

The storage module 450 may include one or more storage devices that are capable of storing data, such as data provided by the image acquisition module 410, the image processing module 420, the control module 430, the display module 440, and/or any other devices. Exemplary types of data that may be stored in the storage devices may include image data, metadata associated with the image data, instruction data, or any other type of data that may be used to implement the method for measuring a pupillary distance in accordance with various embodiments of the present disclosure. In some embodiment, the storage devices may be and/or include a hard disk drive, a solid-state drive, a removable storage drive (e.g., a flash memory disk drive, an optical disk drive, etc.), a digital video recorder, or the like, or a combination thereof.

The components of the user terminal 120 that may be used in connection with the present system described above are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

Figure 5:
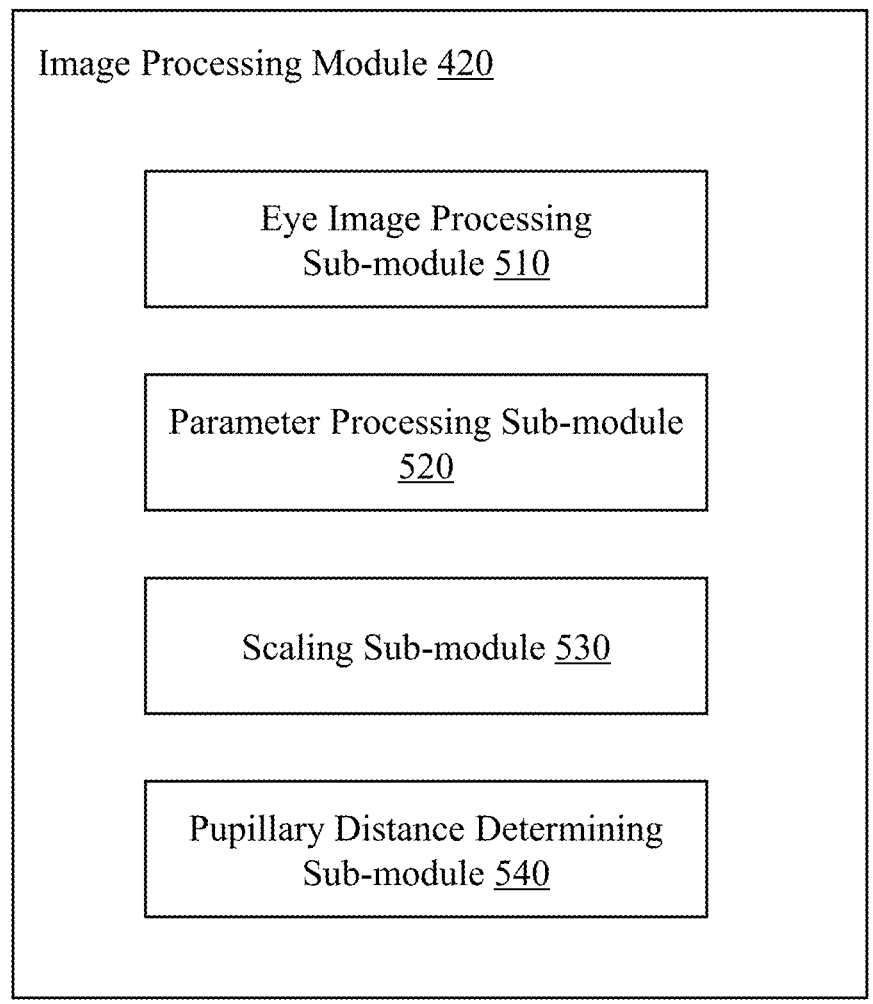
FIG. 5 is a block diagram illustrating an image processing module according to some embodiments of the present disclosure.

FIG. 5 is a block diagram illustrating an image processing module 420 according to some embodiments of the present disclosure. The image processing module 420 may include an eye image processing sub-module 510, a parameter processing sub-module, a scaling sub-module 530, and a pupillary distance determining sub-module 540. The modules included in the image processing module 420 may be connected in a wired or wireless manner. In some embodiments, each head image in a real-time video received by the image acquisition module 410 may be processed based on at least two aspects for recommending a pair of prescription glasses. One of the two aspects may include one or more eye parameters (e.g., pupillary distance, color of pupils, location of eyes, size of eyes, etc.). The other one of the two aspects may include one or more supporting parameters. For example, the width of a face may be used to suggest a frame that fits the width of the face. For another example, the distances between the outer end of the eyes and the ears may be used to suggest a temple length of the glasses. According to the illustrated embodiment, the eye image processing sub-module 510 may be used to process the one or more eye parameters, while the parameter processing sub-module 520 may be used to process the one or more supporting parameters. However, the present disclosure is not intended to be limiting. The eye image processing sub-module 510 and the parameter processing sub-module 520 may be integrated in one sub-module to perform the above described functions.

In some embodiments, the eye image processing sub-module 510 may be configured to process one or more areas within a head image of a person including at least recognized eyes. For example, a rectangular area including components like two eyes, two eyebrows and a nose may be recognized by the eye image processing sub-module 510. Parameters related to the components may be further calculated accordingly. Exemplary parameters may include pupil locations, size and shape of eyes, size of nose, shape of eyebrows, or the like, or a combination thereof. In some embodiments, the parameters related to the components may be used to supplement the prescription. For example, the size and shape of eyes may be used to determine the frame size of the glasses. The size of nose may be used to determine the size of bridge width, or whether nose pads are recommended. The shape of eyebrows may be used to recommend an appropriate style of the glasses. In some embodiments, the pupil locations may be used to direct grinding lenses. Details as to determine the pupil locations by the eye image processing sub-module 510 may be disclosed in FIG. 6.

The parameter processing sub-module 520 may be configured to recognize areas in the head image including one or more supporting parameters, and to further process the recognized areas. For example, for a front view of a head image, a facial outline of the head image may be identified. The width of the face may be determined according to the facial outline. As another example, for a side view of a head image, the distance between the outer end of one eye and the ear on the same side may be determined. In some embodiments, the scale of the one or more supporting parameters determined by the parameter processing sub-module 520 and the scale of the one or more eye parameters determined in the eye image processing sub-module 510 may be a relative scale ratio. Further, a scaling process may be performed to obtain the actual scale of the measured one or more eye parameters and the one or more supporting parameters.

The scaling sub-module 530 may be configured to calculate a plotting scale for the image acquired by the image acquisition module 410. The actual scales of the one or more eye parameters and the one or more supporting parameters may be calculated according to the plotting scale. In some embodiments, the scaling sub-module 530 may calculate the plotting scale according to a plurality of dimension indicators included in the acquired head image. For example, two points indicating an actual distance apart may be included in the head image. A relative distance between the two points in the head image may be determined by the scaling sub-module 530. Corresponding plotting scale may be determined based on the relative distance and the actual distance. In some embodiments, the plurality of dimension indicators may be set in a wearable device. Exemplary wearable device may be a pair of glasses, a ruler, a hat, a headset, or the like, or any devices that may be set close to the head, or a combination thereof. In some embodiments, the material of the wearable devices may be paper and the plurality of dimension indicators are printed on the pair of paper glasses. In some embodiments, the wearable device may be a ruler-like sticker with one or more known scale markers, i.e., dimension indicators. When a person having the ruler-like sticker pasted on his/her forehead performs a self-measurement, the pupillary distance may be directly read from the one or more known scale markers. In some embodiments, the dimension indicators may be marked on the head of the person. For example, two points indicating an actual distance apart may be marked on the face. When taking a photo of the person, the two points may be captured in the photo image and further used to calculate the plotting scale. In some embodiments, the dimension indicators may be marked on one or more stickers. A user may paste the stickers on the user's face part (e.g., forehead). When taking a photo of the user, the dimension indicators may be captured in the photo image and further used to determine the plotting scale.

It should be understood that the examples related to the wearable devices described above are for illustrative purpose. The present disclosure is not intended to be limiting. The material of the wearable device may be any material, for example, metal, plastic, etc. Further, the dimension indictors may be any shape and size, for example, line, arrow, triangle, diamond, icon of a plant, icon of a vegetable, icon of an animal, icon of a person, etc.

The pupillary distance determining sub-module 540 may be configured to determine an actual pupillary distance according to the pupil locations determined by the eye image processing sub-module 510 and the plotting scale determined by the scaling sub-module 530. In some embodiments, a relative pupillary distance may be determined according to the pupil locations recognized from a head image. Further, the actual pupillary distance may be calculated by multiplying the relative pupillary distance with the plotting scale. In some embodiments, the actual pupillary distance may be determined based on the dimension indicators with no need to calculate the plotting scale. For example, when a person wears a pair of paper glasses with high dense dimension indicators with millimeter as a minimum unit, the actual pupillary distance of the person may be estimated directly from the high dense dimension indictors captured in the photo image of the person.

Figure 6:
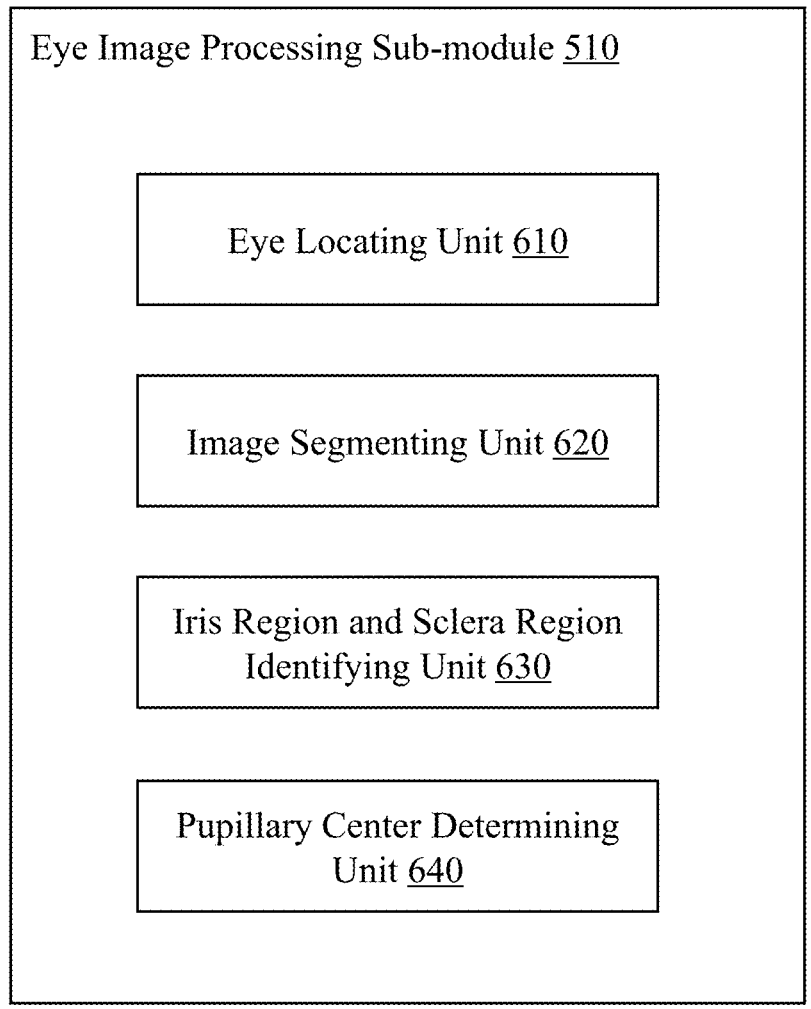
FIG. 6 is a block diagram illustrating an eye image processing sub-module according to some embodiments of the present disclosure.

FIG. 6 is a block diagram illustrating an eye image processing sub-module 510 according to some embodiments of the present disclosure. The eye image processing sub-module 510 may include an eye locating unit 610, an image segmenting unit 620, an iris region and sclera region identifying unit 630 and a pupillary center determining unit 640. The modules included in the eye image processing sub-module 510 may be connected in a wired or wireless manner.

The eye locating unit 610 may be configured to locate eyes of a person in the acquired head image. The eyes may be recognized based on image recognition technology. Exemplary image recognition technology may include a machine learning method, an oriented brief feature extraction algorithm, a scale-invariant feature transform algorithm, or the like, or a combination thereof. The machine learning method may include a Haar feature-based cascade classifier. In some embodiments, a face of the acquired head image may be determined using the Haar feature-based cascade classifier. The eyes on the face may be located based on symmetry information and one or more geometric constraints of different parts of the face. The symmetry information may include the symmetry of two eyes on a face. The geometric constraints may include position and/or size relationships among different parts of the face (e.g., eyes, nose, mouth, etc.). For example, the location of the eyes may be above the nose. In some embodiments, two points may be determined by the eye locating unit 610 to represent the locations of the two eyes. In some embodiments, the wearable devices may be used to assist locating eyes. For example, when a pair of glasses worn by the user is detected and a head image of the user is captured, portions of the head image located inside the frame of the pair of glasses may be considered as the locations of the eyes.

The image segmenting unit 620 may be configured to segment eye images from the head image. As used herein, the eye image may refer to a portion of the head image that contains an entire eye. The segmentation of the eye images may be based on various algorithms. Exemplary segmenting algorithms may include threshold segmentation method, clustering method, histogram-based method, edge detection method, level set method, compression-based method, or the like, or a combination thereof. In some embodiments, the segmentation of the eye images may be based on the eye locations determined by the eye locating unit 610. For example, for a pair of glasses having two near rectangular lens, the two points determined by the eye locating unit 610 that represent the eye locations may be the two centers of the near rectangular lens. The portions of the head image included in the two near rectangular lens may be segmented from the head image for further processing.

The iris region and sclera region identifying unit 630 may be configured to identify the iris region and the sclera region of each eye in the head image. In some embodiments, the identification may be based on the segmented images including eye images. One or more parameters related to the iris and sclera may be used for identification. For example, the identification of the iris region and the sclera region may be based on the color difference of the two regions. From an eye image, a white region may be considered as a sclera region, and a black (dark brown, brown, blue, green or other color for some human race) region may be considered as an iris region. As another example, a bright region in an eye image may be considered as a sclera region, and a darker region in the eye image may be considered as an iris region. In some embodiments, the color based identification method may be assisted by an edge detection method. In some embodiments, a contour of the eye included in the eye image may be recognized first, and the iris region, the sclera region and the pupil are determined using the color based identification. In some embodiments, the color based identification may be based on one or more types of intensity information. For example, for each pixel of the eye image, the grayscale value of the pixel may be one type of intensity information. Pixels with grayscale value within a predetermined range may be considered as located in a corresponding region. For example, pixels with low grayscale value may be considered belonging to a sclera region. All the pixels classified as belonging to a sclera region may form a sclera region in the segmented eye image. In some embodiments, one or two inner edges that separate the iris region and the sclera region may be determined based on the identification. As used herein, the inner edges may refer to the boundary between the iris region and the sclera region which may be used interchangeably with a circular contour of the iris region or an iris circle. The inner edges may be further used for pupil location determination.

The pupillary center determination unit 640 may be configured to determine the pupil location. In some embodiments, the pupil location may be represented by the pupillary center. The pupillary center may be a point in the eye image corresponding to one or more pixels. In some embodiments, the pupillary center may be determined according to the inner edges and the identified sclera region and iris region. Details about the pupillary center determination method may be disclosed elsewhere in the present disclosure (e.g., in the description of FIG. 9).

It should be noted that the above description of the eye image processing sub-module 510 is merely provided for the purposes of illustration, and not intended to limit the scope of the present disclosure. For persons having ordinary skills in the art, multiple variations and modifications may be made under the teachings of the present disclosure. For example, the eye locating unit 610 may be omitted. The image segmenting unit 620 may directly segment eye images from a head image. As another example, the image segmenting unit 620 may be omitted. The iris region and sclera region may be identified directly from the head image.

Figure 7A:
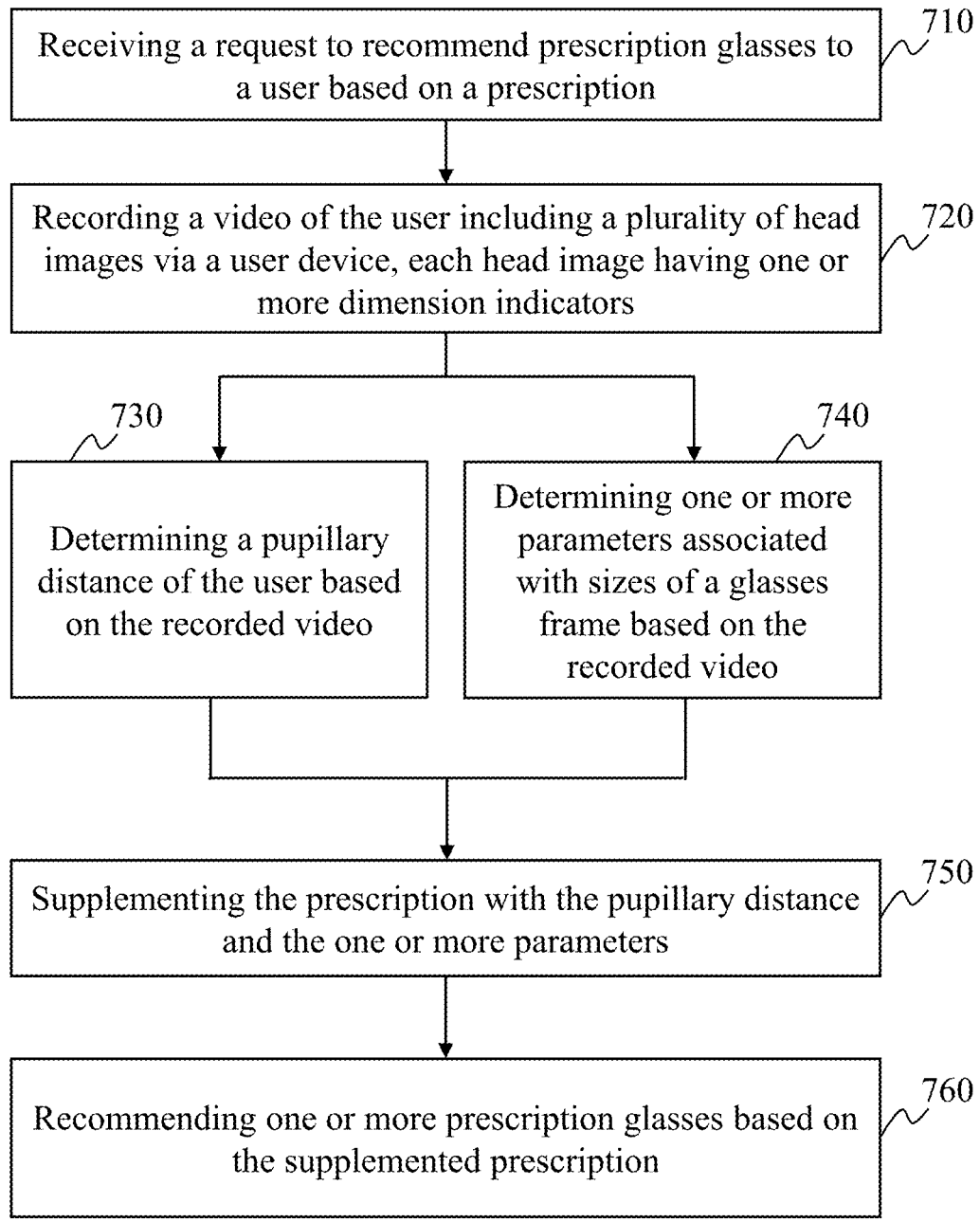
FIG. 7A is a flowchart illustrating a method for providing a prescription glasses according to some embodiments of the present disclosure.

FIG. 7A is a flowchart illustrating a method for providing a prescription glasses according to some embodiments of the present disclosure. In some embodiments, the method may be implemented by the system 100. In some embodiments, the method may apply pupillary distance measurement for recommending prescription glasses.

In step 710, a request to recommend prescription glasses to a user based on a prescription may be received. The request may be transmitted to the server 130 and/or the eyewear distributor 160 via the network 150. In some embodiments, the prescription may not include one or more necessary parameters. Exemplary necessary parameters may include pupillary distance, face width, bridge width, temple length, or the like, or a combination thereof. The prescription may be assessed by the server 130 or the eyewear distributer 160. An instruction that requests for the necessary parameters may be transmitted to the user terminal 120 via the network 150.

In step 720, a video of user including a plurality of head images may be recorded by a user device. In some embodiments, the user device may refer to the user terminal 120. Each of the plurality of head images may have one or more dimension indicators. In some embodiments, the recording may be in response to the request received in step 710. For example, the server 130 or the eyewear distributer 160 may determine that the received prescription is lack of pupillary distance data. A request for the pupillary distance data may be transmitted to a mobile phone, i.e., the user terminal 120. In response to the request, the mobile phone may automatically activate its front camera for recording the user. As another example, the user may initiate the self-measurement of the pupillary distance by controlling the mobile phone to record a video. As used herein, the video may include one or more frames of images. The controlling of the mobile phone to record a video may be implemented via a user interface. For example, the recording of the video may be activated by clicking the "video" button in the camera app of the mobile phone. As another example, the recording of the video may be activated by clicking the "video" button in a mobile app that integrates the camera function. As another example, the recording of the video may be activated by voice recognition app implemented on the mobile phone. The video of the user may record dynamic movements of the user and/or the head of the user. In some embodiments, the head images included in the video may contain different view of the user, such as, a front view and a side view. In some embodiments, the posture of the user may vary. For example, to capture the front view of the head image, the user may need to face to the camera 110 in a predetermined angle. The ratio of the head portion to the entire head image may need to extend a certain percentage. In some embodiments, the dimension indicators may be set on the frame of a wearable device or drawn on the head of the user. Corresponding description of the dimension indicators may be disclosed in the description of the scaling sub-module 530.

In step 730, a pupillary distance of the user may be determined based on the recorded video. If the lacking parameter as indicated by the server 130 or the eyewear distributer 160 is a pupillary distance of a user associated with the received prescription, the user's pupillary distance may be determined in this step. In some embodiments, the pupillary distance determination may be implemented by the image processing module 420. Details about the pupillary distance determination may be disclosed elsewhere in the present disclosure (e.g., in the description of FIG. 76).

In step 740, one or more parameters associated with sizes of a glasses frame may be determined based on the recorded video. In some embodiments, the determination may be implemented by the image processing module 420. The one or more parameters associated with sizes of a glasses frame may include lens width, lens height, bridge width, temple length, or the like, or a combination thereof. In some embodiments, the one or more parameters may be determined based on one or more measurements associated with the head in the captured head image. For example, the temple length may be determined based on the distance between the outer end of the eyes and the ears on the same side of the face. Details about the one or more parameters determination may be disclosed elsewhere in the present disclosure (e.g., in the description of FIG. 7C).

In step 750, the prescription may be supplemented with the pupillary distance and the one or more parameters determined in step 730 and step 740. In some embodiments, the supplementation may be implemented by the user terminal 120. In some embodiments, the supplementation may be implemented by the server 130. The supplemented prescription may be transmitted to the eyewear distributor 160 and/or the database 140.

In step 760, one or more prescription glasses may be recommended based on the supplemented prescription. In some embodiments, the recommending may be implemented by the eyewear distributor 160. In some embodiments, the information of the supplemented prescription may be compared with information associated with a plurality of prescription glasses stored in a glasses database of the eyewear distributor. The result of the comparison may be a plurality of candidate prescription glasses that match the supplemented prescription. The comparison result may be transmitted to the user via the network 150 and the plurality of candidate prescription glasses are displayed on the user terminal 120. Upon receiving a selection of one of the plurality of candidate prescription glasses from the user terminal 120, the eyewear distributor 160 may complete an online order for the selected prescription glasses for the user.

It should be understood that the steps as shown in FIG. 7A is for illustrative purpose, but not intend to limit the protection scope of the present disclosure. In some embodiments, the process may be accomplished with one or more additional steps not described, and/or without one or more of the steps discussed above. Additionally, the order in which the steps of the process as illustrated in FIG. 7A is not intended to be limiting. For example, the video recorded in step 720 may be stored in the data base 140 or the storage module 450, and retrieved in response to a requesting instruction. As another example, the video recorded in step 720 may be substituted by an image, or a frame of the video.

Figure 7B:
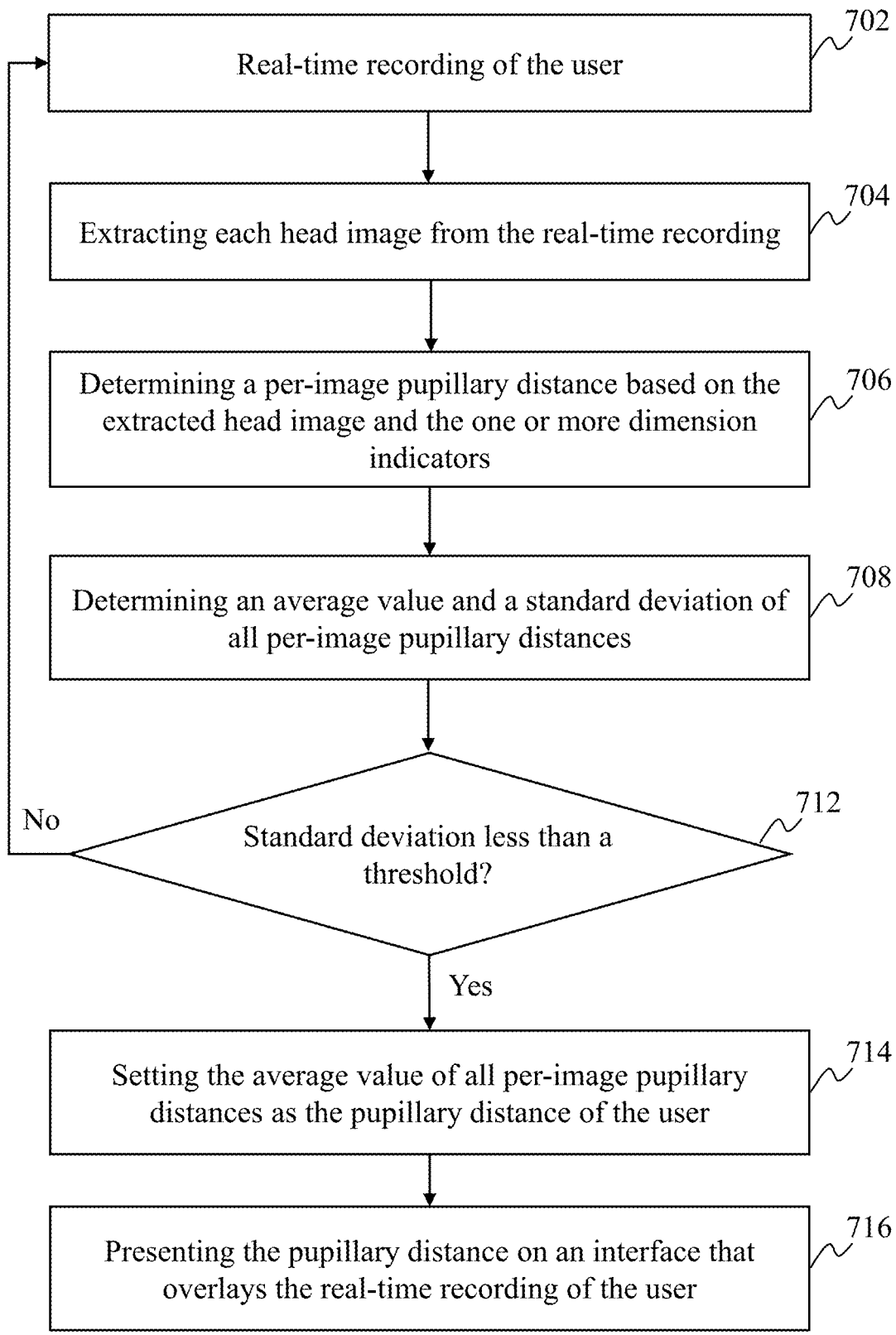
FIG. 7B is a flowchart illustrating a method for determining a pupillary distance of user based on a recorded video according to some embodiments of the present disclosure.

FIG. 7B is a flowchart illustrating a method for determining a pupillary distance of user based on a recorded video according to some embodiments of the present disclosure. In some embodiments, the determination of a pupillary distance may be implemented by the image processing module 420. The recorded video may be processed on a per-images or per-frame basis. The pupillary distance may be determined based on averaging the pupillary distances calculated on the per-image or per-frame basis for all the images or frames in the video.

In step 702, the process may perform a real-time recording of a user. In some embodiments, the real-time recording may be implemented by the camera 110 in response to an instruction transmitted by the user terminal 130. For example, the real time recording may be implemented by a front camera of a mobile phone. The head of the user may need to be included in the real-time recording. The real-time recording may be displayed by the display module 440 synchronously. The user may adjust the posture to ensure that the recording includes a head image.

In step 704, each head image may be extracted from the real-time recording. As used herein, the head image may refer to one or more images in the real-time recorded video, where the head area in the one or more head images may extend a predetermined threshold. For example, 80% area of the head image shows the head of the user.

In step 706, a per-image pupillary distance may be determined based on the extracted head image and the one or more dimension indicators. The pupillary distance determination may be implemented by the pupillary distance determining sub-module 540. For each of the head image extracted in step 704, corresponding pupillary distance may be determined and considered as a per-image pupillary distance. In some embodiments, a part or all of the head images in the real-time recording may be processed to determine the per-image pupillary distance. For example, the head images in the real-time recording may be sampled to calculate the corresponding pupillary distance determinations. Details about the per-image pupillary distance determination based on head image dimension indicators may be disclosed elsewhere in the present disclosure (e.g., in the description of FIG. 8).

In step 708, an average value and a standard deviation of all per-image pupillary distances may be determined. The per-image pupillary distances may be different due to the variations among different head images. During recording, the user posture may not be stable, which causes the differences of the head images. An average value of all the per-image pupillary distances may be calculated to represent real pupillary distance. The standard deviation may represent a degree of differences of all per-image pupillary distances. Exemplary deviation calculation method may include variance method, average deviation method, or the like, or a combination thereof.

In step 712, a determination may be made as to whether the standard deviation is less than a threshold. As disclosed above, the change of user posture may cause differences in the recorded head images, and further cause the differences in the determined per-image pupillary distances. A high standard deviation may indicate that the user posture is not stable during recording. In response to a determination that the standard deviation is less than a threshold, the process may proceed to step 714. On the contrary, in response to a determination that the standard deviation is not less than a threshold, the process may proceed to step 702 to continue real-time recording.

In step 714, the average value of all per-image pupillary distances may be set as the pupillary distance of the user. As the standard deviation is less than the threshold, the user posture may be considered as stable during recording. The average value of all per-image pupillary distances may be used to represent a real pupillary distance of the user. The pupillary distance may be further supplemented to the received prescription.

In step 716, the pupillary distance may be presented on an interface that overlays the real-time recording of the user. A number that indicates the pupillary distance along with a plurality of graphical indicators such as arrows and lines may be displayed above the user's eyes synchronously on the real-time recording interface. The positions of the number and the plurality of graphical indicators may vary in accordance with the movement of the user during recording. In one example, the pupillary distance based on averaging over all images in the real-time recording may be re-calculated due to the user's movement. Thus, the number that indicates the pupillary distance may change on the real-time recording interface. As in another example, if the user's movement does not cause re-calculation of the pupillary distance, the number that indicates the pupillary distance remain unchanged on the real-time recording interface.

It should be understood that the steps as shown in FIG. 7B is for illustrative purpose, but is not intended to limit the protection scope of the present disclosure. In some embodiments, the process may be accomplished with one or more additional steps not described, and/or without one or more of the steps discussed above. Additionally, the order in which the steps of the process as illustrated in FIG. 7B is not intended to be limiting. For example, the real-time recording in step 702 may be replaced by invoking recoding data from a database. For another example, step 708 may be separated into two steps with respect to average value calculation and standard deviation calculation.

Figure 7C:
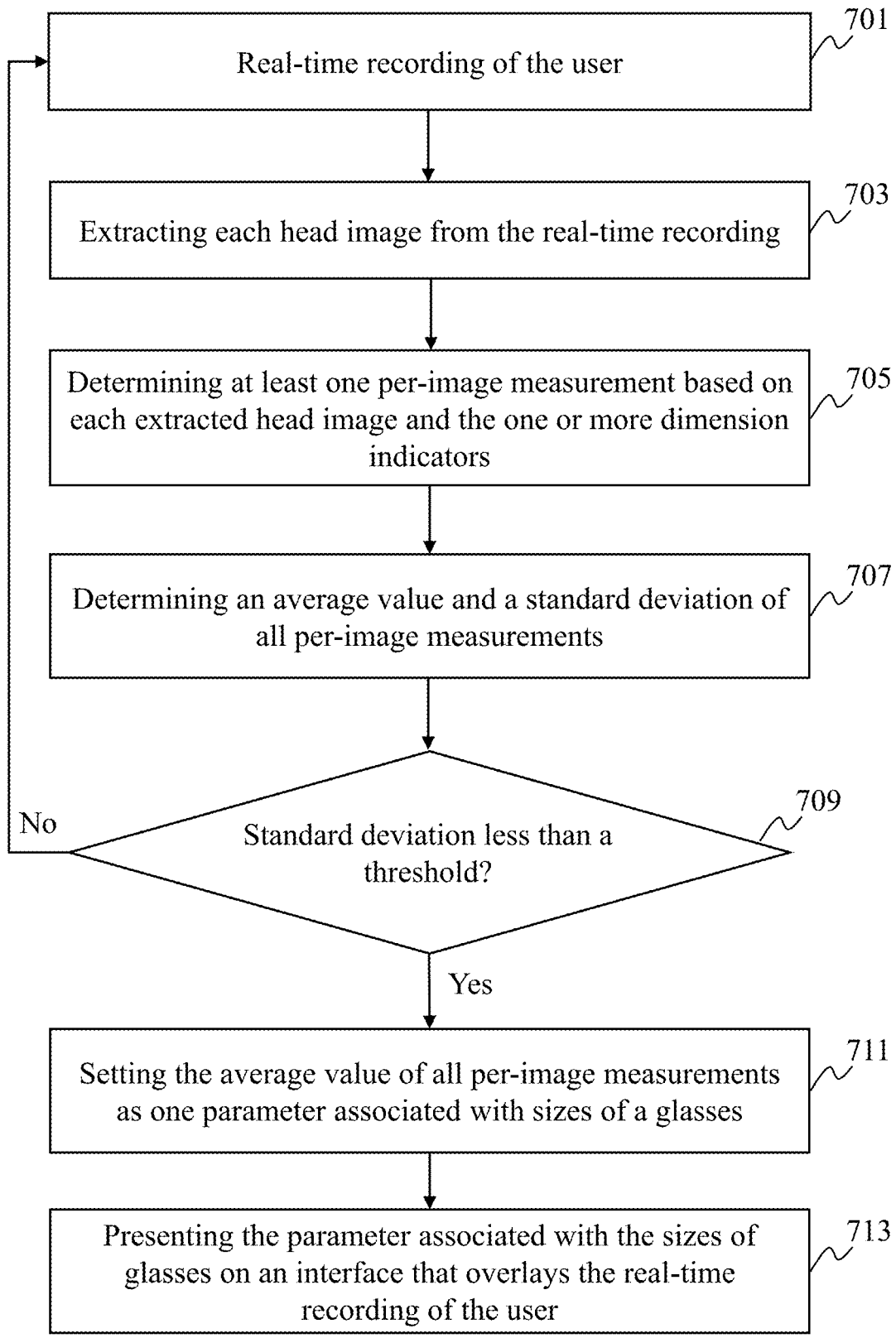
FIG. 7C is a flowchart illustrating a method for determining one parameter associated with sizes of glasses based on a recorded video according to some embodiments of the present disclosure.

FIG. 7C is a flowchart illustrating a method for determining one parameter associated with sizes of glasses based on a recorded video according to some embodiments of the present disclosure. In some embodiments, the determination may be implemented by the image processing module 420. The determination method may also apply to the per-image process as disclosed in FIG. 7B. The parameters associated with sizes of glasses may also be determined based on the per-image calculation.

In step 701, the process may perform a real-time recording of a user. The recording method may be similar to step 702 of FIG. 7B. In some embodiments, the recording may require the user to keep a different posture from that in step 702. For example, if the parameter is the distance between the outer end of the eye and the ear on the same side of the face, the user may stand showing a side face to the camera 110.

In step 703, each head image may be extracted from the real-time recording. The extracting method may be similar to the step 704 of FIG. 7B.

In step 705, at least one per-image measurement may be determined based on each extracted head image. In some embodiments, the at least one per-image measurement may be used as one parameter associated with sizes of a glasses. Exemplary parameters associated with sizes of a glasses frame may include lens width, lens height, bridge width, temple width, or the like, or a combination thereof. The per-image measurement determination may be similar to the per-image pupillary distance determination.

In step 707, an average value and a standard deviation of all per-image measurements may be determined. The definition and determination method may be similar to the per-image pupillary distances in step 712 of FIG. 7B.

In step 709, a determination is made as to whether the standard deviation is less than a threshold. If it is determined that the standard deviation is less than a threshold, the process may proceed to step 711. On the contrary, if the stand deviation is determined no less than the threshold, the process may proceed to step 701 to continue recording as the user posture may be considered as not stable.

In step 711, the average value of all per-image measurements may be set as one parameter associated with sizes of glasses. The parameter may be further supplemented to the received prescription.

In step 713, the parameter associated with the sizes of glasses may be presented on an interface that overlays the real-time recording of the user. A number that indicates the parameter along with a plurality of graphical indicators such as arrows and lines may be displayed synchronously on the real-time recording interface. For example, the right temple width of the user may be displayed on the side face. The positions of the number and the plurality of graphical indicators may vary in accordance with the movement of the user during recording. In one example, the parameter based on averaging over all images in the real-time recording may be re-calculated due to the user's movement. Thus, the number that indicates the parameter may change on the real-time recording interface. As in another example, if the user's movement does not cause re-calculation of the parameter, the number that indicates the parameter remain unchanged on the real-time recording interface.

It should be understood that the steps as shown in FIG. 7C is for illustrative purpose, but is not intended to limit the protection scope of the present disclosure. In some embodiments, the process may be accomplished with one or more additional steps not described, and/or without one or more of the steps discussed above. Additionally, the order in which the steps of the process as illustrated in FIG. 7C is not intended to be limiting.

Figure 8:
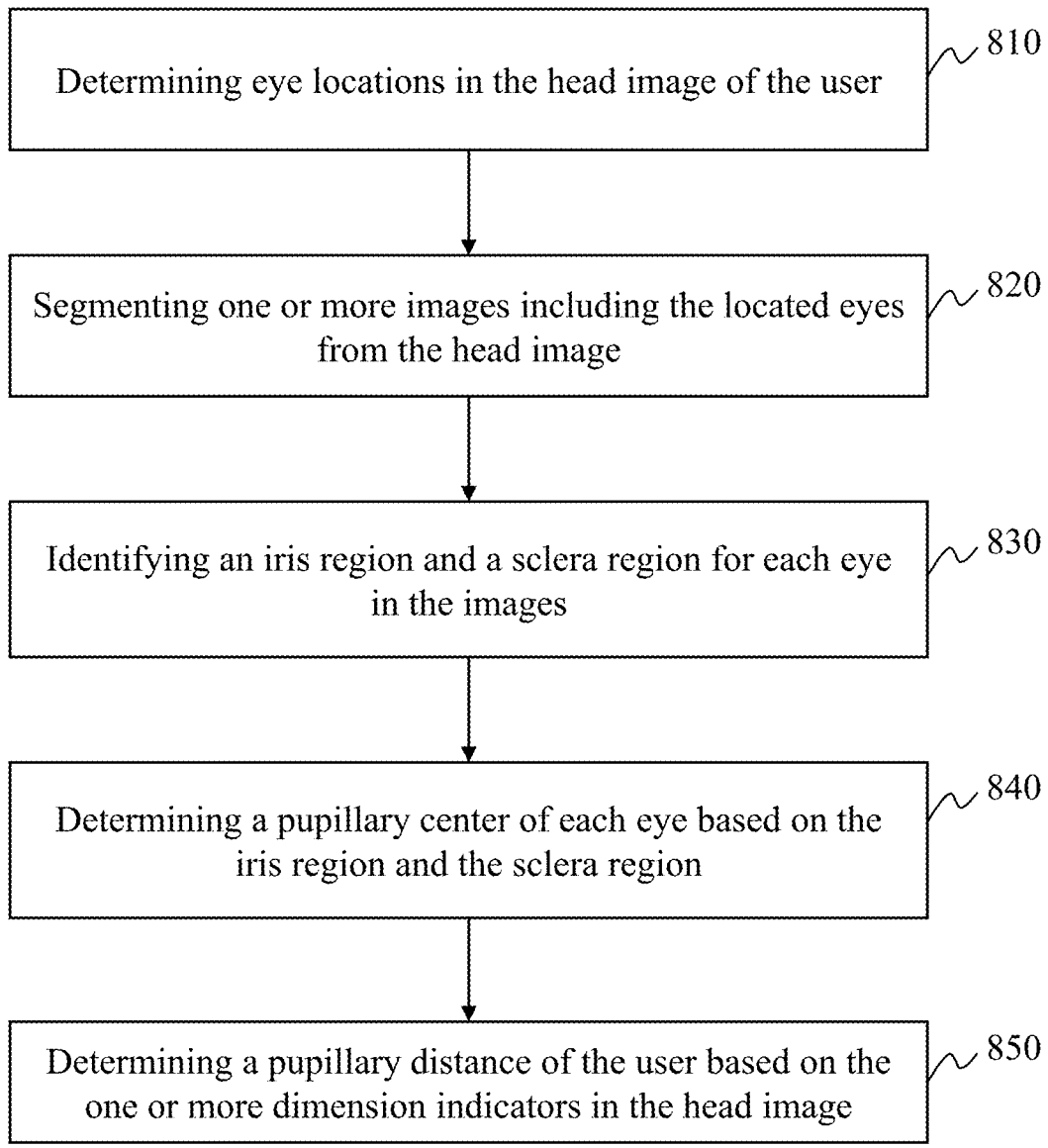
FIG. 8 is a flowchart illustrating a method for determining a per-image pupillary distance based on head image and dimension indicators according to some embodiments of the present disclosure.

FIG. 8 is a flowchart illustrating a method for determining a per-image pupillary distance based on head image and dimension indicators according to some embodiments of the present disclosure. The process may be implemented by the eye image processing sub-module 510 and the pupillary distance determining sub-module 540.

In step 810, eye locations in the head image of the user may be determined. In some embodiments, the determination may be implemented by the eye locating unit 610. In some embodiments, the head image may refer to the per-image disclosed in FIG. 7A, FIG. 7B, and FIG. 7C. The eyes of the user may be recognized based on image recognition technology. In some embodiments, two points may be determined to represent the locations of the two eyes. In some embodiments, wearable devices may be used to locate the eyes. Related description may be disclosed in the description of eye locating unit 610.

In step 820, one or more images including the located eyes may be segmented from the head image. In some embodiments, the segmentation may be implemented by the image segmenting unit 620. The image including located eyes may refer to the eye image. In some embodiments, one eye image may include one of the two eyes. In some embodiments, the segmentation may be based on the eye locations determined in step 810. Related segmentation method may be similar to the description of image segmenting unit 620.

In step 830, an iris region and a sclera region for each eye may be identified from the one or more images. In some embodiments, the identification may be implemented by the iris region and sclera region identifying unit 630. Related description about the identification may be disclosed in the description of iris region and sclera region identifying unit 630. In some embodiments, for each eye, one or two inner edges that separate the iris region and the sclera region may be determined based on the identification. The inner edges may be further used for pupil location determination.

In step 840, a pupillary center of each eye may be determined based on the iris region and the sclera region. In some embodiments, the determination may be implemented by the pupillary center determination unit 640. In some embodiments, the determination based on the iris region and the sclera region may refer to determination based on the inner edges. Detailed description may be disclosed in FIG. 9.

In step 850, a pupillary distance of the user may be determined based on the one or more dimension indicators. In some embodiments, the determination may be implemented by the pupillary distance determining sub-module 540. Related description may be disclosed in the description of pupillary distance determining sub-module 540.

It should be understood that the steps as shown in FIG. 8 is for illustrative purpose, but is not intended to limit the protection scope of the present disclosure. In some embodiments, the process may be accomplished with one or more additional steps not described, and/or without one or more of the steps discussed above. Additionally, the order in which the steps of the process as illustrated in FIG. 8 is not intended to be limiting.

Figure 9:
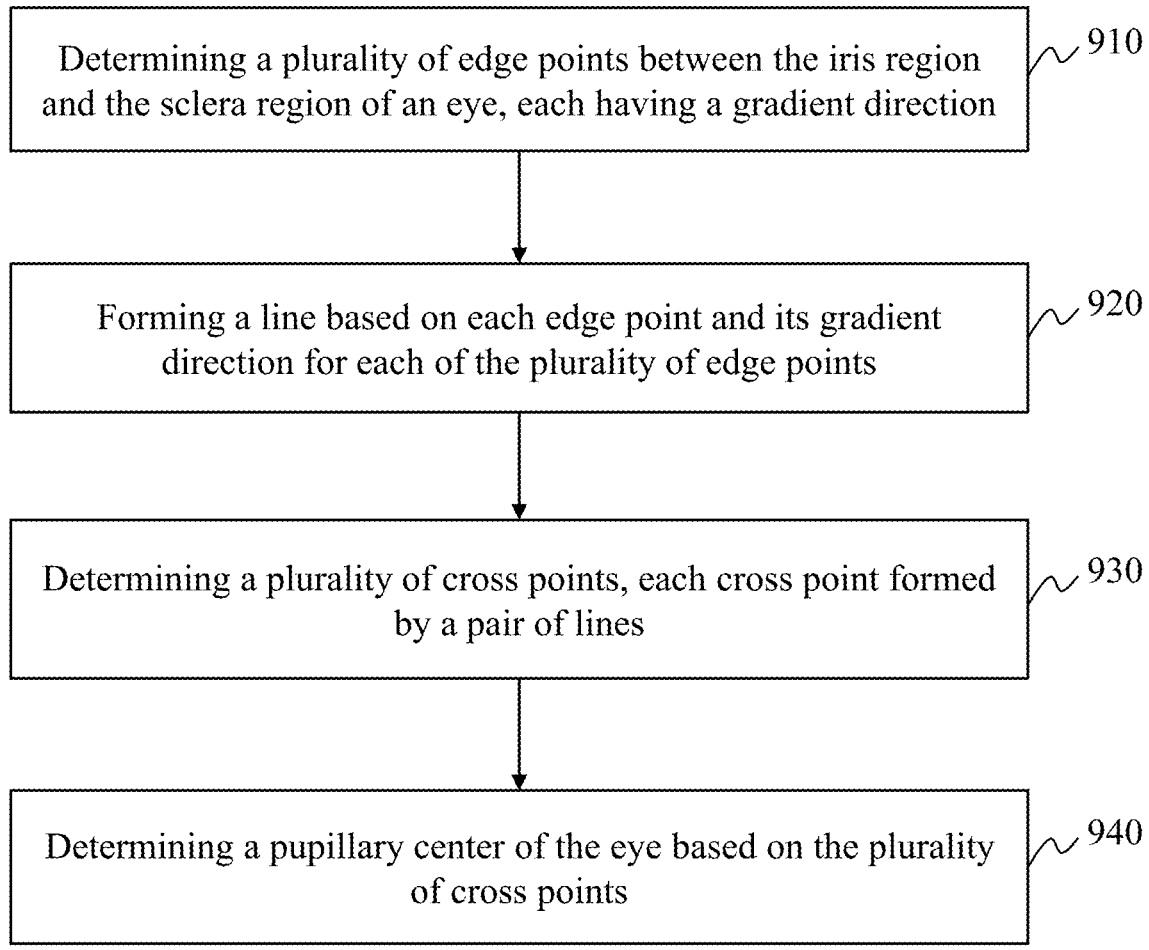
FIG. 9 is a flowchart illustrating a method of determining a pupillary center based on the iris region and the sclera region according to some embodiments of the present disclosure.

FIG. 9 is a flowchart illustrating a method of determining a pupillary center based on the iris region and the sclera region according to some embodiments of the present disclosure. In some embodiments, the determination may be implemented by the pupillary center determining unit 640.

In step 910, a plurality of edge points between the iris region end the sclera region of an eye may be determined. Each of the edge points has a gradient direction. In some embodiments, the gradient may refer to the gradient of the one or more types of intensity information that used in the color based identification to separate the iris region and the sclera region. For example, grayscale value may be used as the intensity information. The gradient direction may be a direction that shows the change of the grayscale values close to an edge point. In some embodiments, the plurality of edge points may be determined based on the inner edges disclosed above. For example, the inner edges may be discretized into a plurality of discrete points. The discrete points may be considered as the edge points.

In step 920, a line may be formed based on each edge point and its gradient direction for each of the plurality of edge points. In some embodiments, the line may be a straight line with an arrow indicating a corresponding gradient direction that travels though the sclera region and the iris region.

In step 930, a plurality of cross points may be determined. Each cross point may be formed by a pair of lines. A cross point may be determined by two unparallel straight lines in a two-dimensional space. By choosing two edge points to form a cross point via the associated gradient directions, the cross point may fall into the pupil region. In some embodiments, the choosing of two edge points to form a cross point may be determined based on a criteria. For example, an angle formed by two gradient directions associated with two edge points may be used as one criteria. The angle may be assessed to determine whether to filter the corresponding cross point. In some embodiments, a value range of the angle may be determined to assess the angle. For example, an obtuse angle greater than 120 degrees may be used as the value range to filter the cross point.

In step 940, a pupil center of the eye may be determined based on the plurality of cross points. In some embodiments, one of the plurality of cross points may be determined as the pupil center. Detail description about this type of determination may be disclosed in FIG. 14A and FIG. 14C. In some embodiments, a new point may be determined based on the distribution of the plurality of cross points and considered as the pupil center. Detail description about this type of determination may be disclosed in FIG. 14B.

It should be understood that the steps as shown in FIG. 9 is for illustrative purpose, but is not intended to limit the protection scope of the present disclosure. In some embodiments, the process may be accomplished with one or more additional steps not described, and/or without one or more of the steps discussed above. Additionally, the order in which the steps of the process as illustrated in FIG. 9 is not intended to be limiting.

Figure 10:
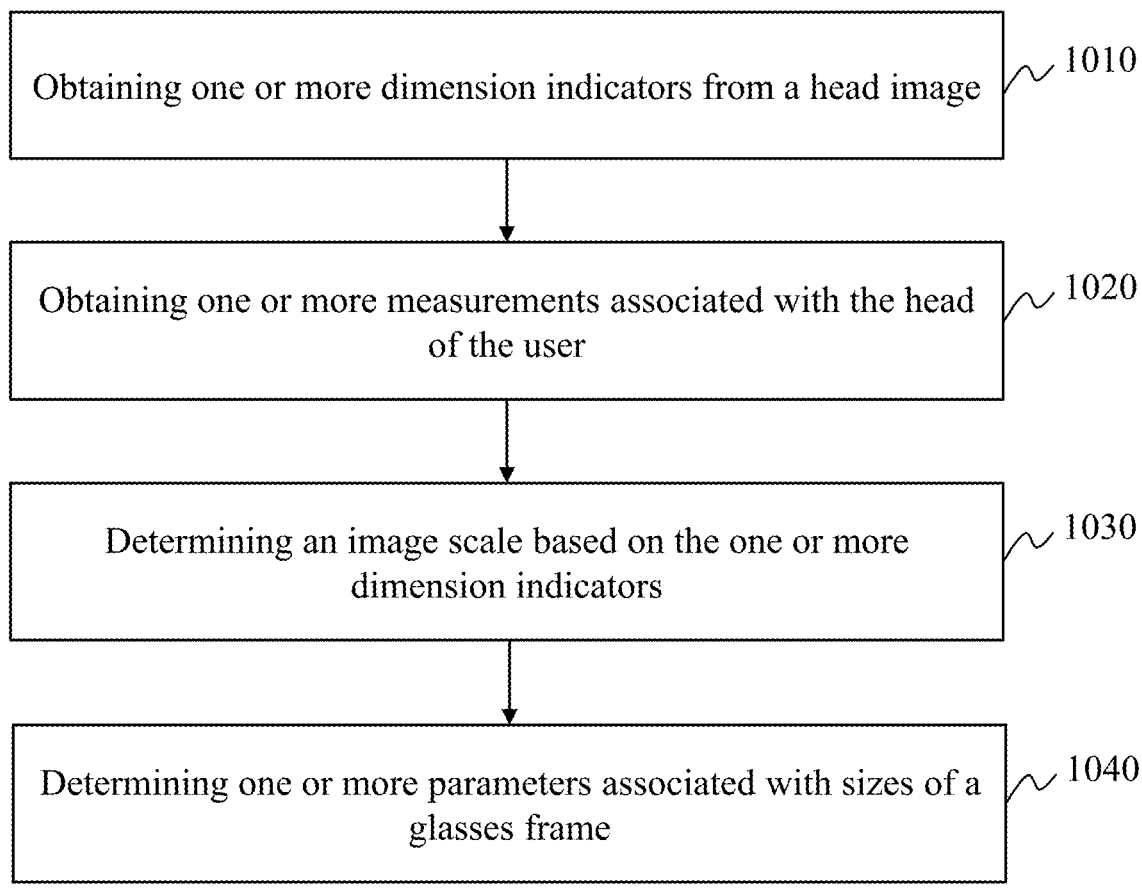
FIG. 10 is a flowchart illustrating a method for determining parameters associated with sizes of a glass frame based on dimension indicators according to some embodiments of the present disclosure.

FIG. 10 is a flowchart illustrating a method for determining parameters associated with sizes of a glass frame based on dimension indicators according to some embodiments of the present disclosure.

In step 1010, one or more dimension indicators may be obtained from a head image. The dimension indicators may be set in a wearable device or drawn on the head as disclosed in the description of scaling sub-module 530. The obtaining may implemented by the parameter processing sub-module 520.

In step 1020, one or more measurements associated with the head of the user may be obtained. The obtaining may be implemented by the parameter processing sub-module 520. The measurements may be used as one or more parameters associated with sizes of a pair of glasses. Exemplary parameters associated with sizes of a glasses frame may include lens width, lens height, bridge width, temple width, or the like, or a combination thereof. In some embodiments, the one or more measurements are relative values and need to be transformed in to actual values via a plotting scale.

In step 1030, an image scale may be determined based on the one or more dimension indictors. In some embodiments, the image scale may refer to the plotting scale disclosed in the description of scaling sub-module 530. The image scale may represent the proportional relationship between the relative value measured with respect to the head image and actual sizes with respect to the head. Related description about determining image scale may be disclosed in the description of scaling sub-module 530.

In step 1040, one or more parameters associated with sizes of glasses may be determined. In some embodiments, the one or more parameters associated with sizes of glasses may be determined based on the one or more measurements and the image scale. For example, a measurement may be a distance between the outer end of the eye and the ear on the same side of the face. A temple length may be determined by multiplying the measurement and the image scale.

It should be understood that the steps as shown in FIG. 10 is for illustrative purpose, but is not intended to limit the protection scope of the present disclosure. In some embodiments, the process may be accomplished with one or more additional steps not described, and/or without one or more of the steps discussed above. Additionally, the order in which the steps of the process as illustrated in FIG. 10 is not intended to be limiting.

Figure 11A:
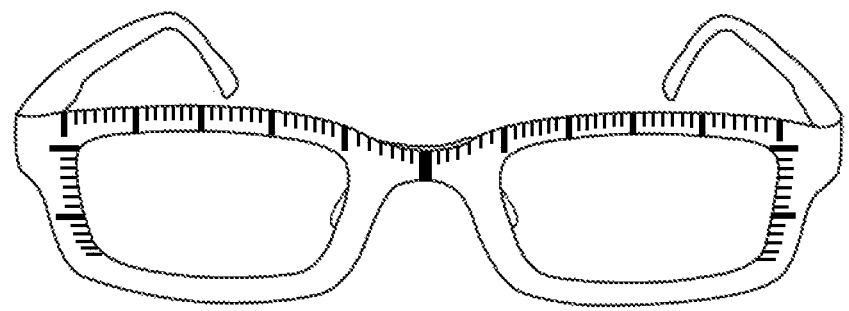
FIG. 11A and FIG. 11B are two examples of wearable devices with dimension indicators according to some embodiments of the present disclosure.
Figure 11B:
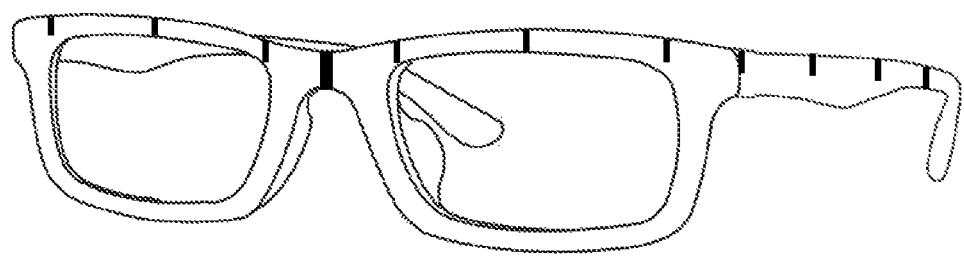

FIG. 11A and FIG. 11B are two examples of wearable devices with dimension indicators according to some embodiments of the present disclosure. In some embodiments, the wearable device may be a pair of glasses. The material of the wear device may be paper, plastic, metal, or the like, or a combination thereof. In some embodiments, a paper glasses may be made by paper with certain thickness. The paper glasses may include a frame with a plurality of dimension indicators printed on the top, nose bridge, or side legs of the frame. In some embodiments, the paper glasses may also include lens made of paper, plastic, metal, or other materials. When the camera 110 records a head image of the user wearing the paper glasses, the dimension indicators may also be captured. An image scale may be determined based on the dimension indicators captured on the head image.

In some embodiments, as illustrated in FIG. 11A, the glasses like wearable device may include a plurality of dense markers distributed on the frame. A center marker may be located in the center of the glasses like wearable device. In addition, other dense markers may be printed as short and narrow markers and separated by one or more long and thick markers. The long and thick markers may represent a first measurement unit. The short and narrow markers may represent a second measurement unit. For example, the first measurement unit may be centimeter and the second measurement unit may be millimeter. For the glasses like wearable device with the dense markers, image scale may not be essential during the pupillary distance measuring. After the determination of the pupillary center, the location of the pupillary center and further the pupillary distance may be read directly based on the dense markers.

In some embodiments, as illustrated in FIG. 11B, the glasses like wearable device may include a plurality of sparse markers distributed on the frame. Unlike the dese markers shown in FIG. 11A, for the glasses like wearable device with sparse markers, the location of a pupillary center and further the pupillary distance may be difficult to read directly based on the sparse markers. As such, the image scale may need to be determined based on the sparse markers captured in the real-time recording. For example, as the distance between two sparse markers may be a predetermined value, by comparing a relative distance value obtained from the head image with the predetermined value between the corresponding two sparse markers, the image scale may be determined. In addition, markers (both dense markers and sparse markers) may be distributed on the legs of the glasses like wearable device. In this case, an image scale corresponding to a side view of the head image may be determined accordingly.

It should be understood that the glasses like wearable device as shown in FIGS. 11A and 11B is for illustrative purpose, but is not intended to limit the scope of the present disclosure. In some embodiments, the wearable device may include a ruler-shaped device, a hat or helmet like wearable device, a wearable sheet made of any material that can be attached to the skin, etc. In addition, the wearable device may be made in any color and/or with any patterns on the frame. Further, the markers shown in FIGS. 11A and 11B are for illustrative purpose only. In some embodiments, the markers can be any type of styles including but not limited to straight line, arrow, pointer, dot, star, triangle, diamond, hexagon, any icon of a plant, any icon of an animal, any icon of a universe object, etc.

Figure 12A:
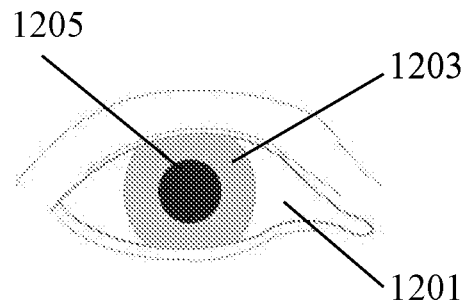
FIG. 12A and FIG. 12B are two examples of eye images according to some embodiments of the present disclosure.
Figure 12B:
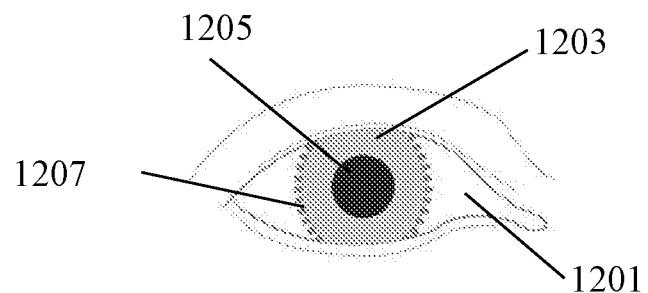

FIG. 12A and FIG. 12B are two examples of eye images according to some embodiments of the present disclosure. The eye images may be segmented from a head image. The eye image may include a sclera region 1201, an iris region 1203, and a pupil region 1205.

In some embodiments, as illustrated in FIG. 12A, different regions (e.g., sclera region 1201, iris region 1203, and pupil region 205) of the eye may be identified based on intensity information. For example, sclera region 1201 may be bright and flat regions. Iris region 1203 may be a darker region between two parts of sclera region 1201. Pupil region 205 may be a darkest region at the center of the eye.

In some embodiments, as illustrated in FIG. 12B, an inner edge 1207 between the sclera region 1201 and the iris region 1203 may be identified. A plurality of edge points on the edge may be determined.

Figure 13:
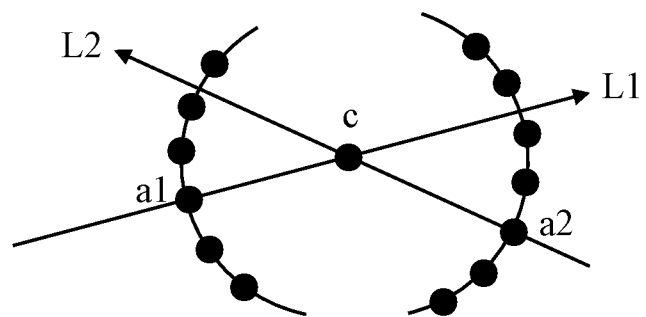
FIG. 13 is a schematic diagram illustrating an example of determining a cross point according to some embodiments of the present disclosure.

FIG. 13 is a schematic diagram illustrating an example of determining a cross point according to some embodiments of the present disclosure. As illustrated in FIG. 13, $a1$ and $a2$ may be two edge points on the inner edges between the sclera region and the iris region. A line $L1$ may be determined based on $a1$ and the gradient direction of $a1$. A line $L2$ may be determined based on $a2$ and the gradient direction of $a2$. A cross point $c$ may be determined by Line $L1$ and line $L2$.

Figure 14A:
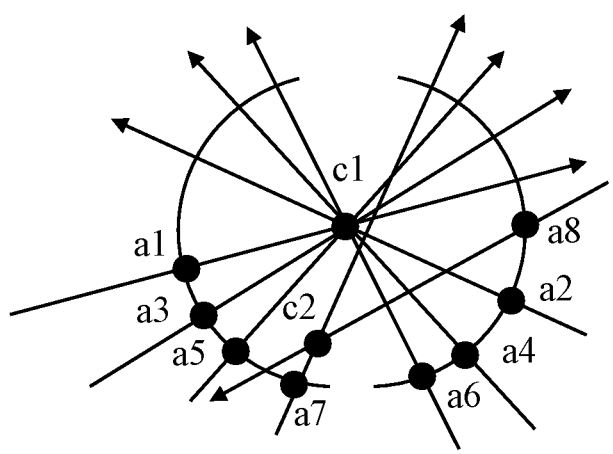
FIG. 14A, FIG. 14B and FIG. 14C are three examples of determining a pupillary center of an eye according to some embodiments of the present disclosure.
Figure 14B:
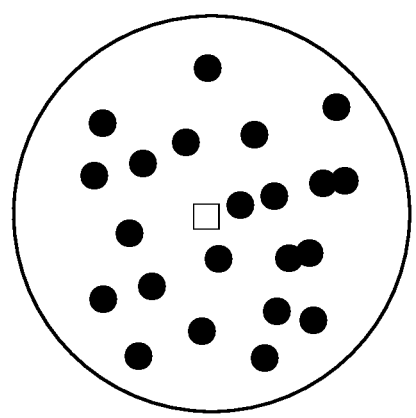
Figure 14C:
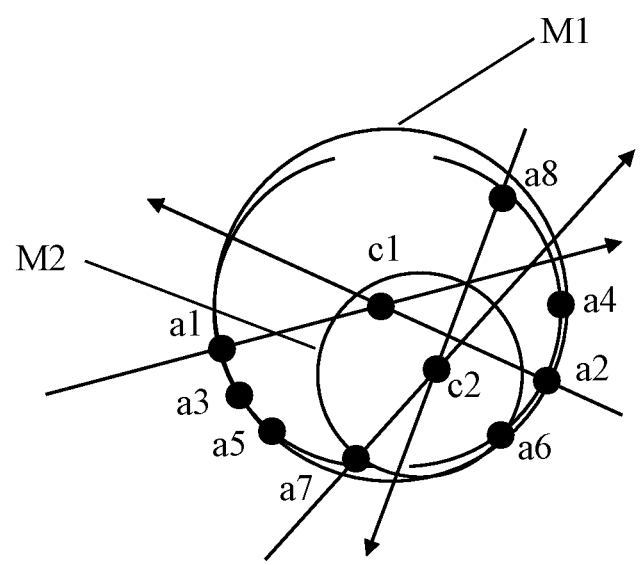

FIG. 14A, FIG. 14B and FIG. 14C are three examples of determining a pupillary center of an eye according to some embodiments of the present disclosure.

As illustrated in FIG. 14A, a cross point corresponding to the largest number of edge points may be considered as the pupillary center of the eye. For example, $c1$ and $c2$ may be two cross points. $c1$ may be the cross point of three pair of lines formed by edge points $a1$, $a2$, $a3$, $a4$, $a5$, and $a6$, respectively. $c2$ may be the cross point of one pair of line formed by edge points $a7$ and $a8$. Cross point $c1$ may be determined as the pupillary center of the eye. In some embodiments, $c1$ may be an estimated center of one or more cross points that are within a predetermined range.

As illustrated in FIG. 14B, a plurality of cross points (shown as black dots) may be distributed randomly within the iris region. A circle with a minimum radius may be drawn to represent the distribution range of the cross points. The center of the circle (shown as a square box) may be determined as the pupillary center of the eye.

As illustrated in FIG. 14C, for each cross point, a circle may be determined centered at the cross point. The radius of the circle may be a distance from the cross point to one of the two corresponding edge points. The pupillary center of the eye may be determined to be the center of a circle that covers the largest number of edge points.

For example, cross point $c1$ may correspond to edge points $a1$ and $a2$. Cross point $c2$ may correspond to edge points $a7$ and $a8$. A circle $M1$ may be determined. The center of $M1$ may be cross point $c1$, and the radius of $M1$ may be the distance from $c1$ to $a1$. A circle $M2$ may be also determined. The center of $M2$ may be cross point $c2$, and the radius of $M2$ may be the distance from $c2$ to $a7$. Edge points $a1$, $a2$, $a3$, $a4$, $a5$, and $a6$ may be distributed on $M1$. Edge points $a6$ and $a7$ may be distributed on $M2$. Therefore, cross point $c1$ may be determined to be the pupillary center of the eye. After a certain number of the cross points are processed in this method. The most appropriate circle may be determined, and the corresponding cross point may be determined as the pupillary center of the eye.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

I claim:

1. A method implemented on a computing device having at least one processor, storage, and a communication platform connected to a network, comprising:
    obtaining multiple head images of a user with one or more dimension indicators;
    for each of the multiple head images,
    determining an eye region in the head image of the user; and
    determining a per-image pupillary distance of the user based on the one or more dimension indicators and the determined eye region, including:
        locating an eye image including two eyes in the head image of the user;
        segmenting the eye image from the head image of the user;
        identifying an iris region and a sclera region for each eye in the eye image;
        determining a plurality of edge points between the iris region and the sclera region for each eye, each of the plurality of edge points corresponding to a gradient direction;
        forming a line based on each of the plurality of edge points and the gradient direction corresponding to each of the plurality of edge points;
        determining a plurality of cross points, each cross point formed by a pair of lines; and
        determining a pupillary center based on the plurality of cross points;
    determining an average value and a standard deviation of all per-image pupillary distances;
    determining whether the standard deviation is less than a threshold; and
    determining the average value as the pupillary distance of the user in response to determining that the standard deviation is less than the threshold.

2. The method of claim 1, further comprising:
    obtaining one or more measurements associated with the head from the head of the user;
    determining an image scale based on the one or more dimension indicators and the one or more measurements; and
    determining one or more parameters associated with sizes of a glasses frame.

3. The method of claim 2, wherein the one or more measurements comprises at least one of a width of face or a distance between an outer end of each eye and an ear on the same side of the face.

4. The method of claim 2, wherein the determining the image scale based on the one or more dimension indicators and the one or more measurements comprises:
    determining information associated with the one or more dimension indicators; and
    determining the image scale based on the information of the one or more dimension indicators and the one or more measurements,
    wherein the information associated with the one or more dimension indicators includes at least one of color information and symmetry information.

5. The method of claim 1, wherein the one or more indicators are implemented on a wearable device worn by the user.

6. The method of claim 5, wherein the wearable device includes a pair of glasses made of paper.

* * * * *